(12) United States Patent
Zhang et al.

(10) Patent No.: US 7,374,939 B1
(45) Date of Patent: May 20, 2008

(54) METHOD OF INACTIVATION OF AN END PRODUCT OF ENERGY METABOLISM IN ZYMOMONAS MOBILIS

(75) Inventors: Min Zhang, Lakewood, CO (US); Yat-Chen Chou, Lakewood, CO (US)

(73) Assignee: Midwest Research Institute, Kansas City, MO (US)

( * ) Notice: Subject to any disclaimer, the term of this patent is extended or adjusted under 35 U.S.C. 154(b) by 0 days.

(21) Appl. No.: 09/562,613

(22) Filed: May 1, 2000

(51) Int. Cl.
*C12N 15/74* (2006.01)
*C12N 15/00* (2006.01)
*C12N 1/20* (2006.01)

(52) U.S. Cl. ............... 435/471; 435/320.1; 435/252.3

(58) Field of Classification Search ............... 435/6, 435/320.1, 91.4, 471, 476, 477, 252.3; 536/23.1
See application file for complete search history.

(56) References Cited

U.S. PATENT DOCUMENTS

| | | | |
|---|---|---|---|
| 5,514,583 A | 5/1996 | Picataggio | |
| 5,712,133 A | 1/1998 | Picataggio | |
| 5,726,053 A | 3/1998 | Picataggio | |
| 5,843,760 A | 12/1998 | Zhang | |

FOREIGN PATENT DOCUMENTS

| | | |
|---|---|---|
| WO | WO/01/183786 | 11/2001 |
| WO | WO 0183786 A2 | 11/2001 |

OTHER PUBLICATIONS

Pappas, K. M., et al., Transposon mutagenesis and strain construction in *Zymomonas mobilis*, Journal of Applied Microbiology 82:379-388, 1997.
DeLorenzo, V., et al., Mini-Tn5 Transposon Derivatives for Insertion Mutagenesis, Promoter Probing, and Chromosomal Insertion of Cloned DNA in Gram-negative Eubacteria, Journal of Bacteriology, vol. 172, No. 11, p. 6568-6572, 1990.
Herrero, M., et al., Transposon Vectors Containing Non-Antibiotic Resistance Selection Markers for Cloning and Stable Chromosomal Insertion of Foreign Genes in Gram-negative Bacteria, Journal of Bacteriology, vol. 172, No. 11, p. 6557-6567, 1990.
Fellay, R., et al., Interposon mutagenesis of soil and water bacteria a family of DNA fragments designed for in vitro insertional mutagenesis of Gram-negative bacteria, Gene, vol. 52., pp. 147-154, 1987.
Dodson, Karen W., et al., Factors affecting transposition activity of IS50 and Tn5 ends, Gene, vol. 76, pp. 207-213, 1989.
Auerswald, E.A., et al., Structural analysis of Tn5, Cold Spring Harbor Symp. Quant. Biol. vol. 45 pp. 107-113, 1980.
Yomano, L.P., et al., Cloning, sequencing, and expresssion of the *Zymomonas mobilis* phosphoglycerate mutase gene (pgm) in *Escherichia coli*, Journal of Bacteriology, vol. 175, pp. 3926-3933, 1993.

Deanda, K.A., et al., Development of an arabinose-fermenting *Zymomonas mobilis* strain by metabolic pathway engineering, Journal of Applied and Environmental Microbiology, vol. 62, pp. 4465-4470, 1996.
Zhang, K., et al., Metabolic engineering of a pentose metabolism pathway in ethanologenic *Zymomonas mobilis*, Science, vol. 267, pp. 240-243, 1995.
Chou, Y.C. et al. "Inactivation of the D-Lactate Dehydrogenase Gene in *Zymomonas mobilis* Through Homologous Recombination"; Abstracts of the General Meeting of the American Society for, vol. 99, 1999, p. 370; XP0001037633; 99th General Meeting of the American Society for Microbiology; Chircago, Illinois, USA; May 30-Jun. 3, 1999, 1999 ISSN: 1060-2011 the whole document.
Zhang, M. et al.; Improve Zymomonas for Xylose and arabinose fermentation:; Database Internet 'Online!; US Department of Energy, Office of Fuel Development; http://bioenergy.ornl.gov/99summaries/, Mar. 2000 XP002185662.
Bunch, P.K. et al.; "The IdhA gene encoding the fermentative lactate dehydrogenase of *Escherichia coli*"; Microbiology, Society for General Microbiology, Reading, GB; vol. 143, 1997, pp. 187-195; XP000996645; ISSN: 1350-0872.
Yomano, Lorraine, P. et al. Cloning, Sequencing and Expression of the *Zymomonas mobilis* Phosphoglycerate Mutase Gene (pgm) in *Escherichia coli*; Journal of Bacterialology; vol. 175, No. 13, 1993, pp. 3926-3933; XP001022915; ISSN: 0021-9193; p. 3930.
Yomano, L.P. et al; Database EMBL 'Online! retrieved from Database accession No. L09650; XP002185663 (1993).
Deanda, Kristine et al.; "Development of an Arabinose-Fermenting *Zymomonas mobilis* Strain by Metabolic Pathway Engineering"; Washington, D.C., U.S.; vol. 62, No. 12, Dec. 1996, pp. 4465-4470; XP002912122; ISSN: 0099-2240.
Lawford, Hugh G., "Conditions that Promote Production of Lactic Acid by *Zymomonas mobilis* in Batch and Continuous Culture"; Applied Biochemistry and Biotechnology; vol. 70-72, Apr. 1, 1998, pp. 173-185, XP001037012; ISSN: 0273-2289.
Chou, Y C et al, Inactivation of the D-lactate dehydrogenase gene in Zymomonas mobilis through homologous recombination Abstracts of the General Meeting of the Amer. Soc. for Microbiology, May 30-Jun. 3, 1999, p. 370, v 99, Chicago, IL.
Zhang, M. et al, Improve Zymomonas for xylose and arabinose fermentation, http://bioenergy.oml.gov.99summaries, Mar. 2000, database internet US DOE, Ofc of Fuel Development.
Bunch, P K et al, The idha gene encoding the fermentative lactate dehydrogenase of escherichia coli, Microbiology, Society for General Microbiology, 1997, pp. 187-195, v 143, Reading, GB.
Yomano, L P et al, Cloning, sequencing, and expression of the Zymomons mobilis phospoglycerate mutase gene (pgm) in Escherichia coli, Journal of Bacteriology, 1993, pp. 3926-3933, v 175 #13.
Deanda, K et al, Development of an arabinose-fermenting zymomonas mobilis strain by metabolic pathway engineering, Applied & Environmental Microbiology, 1996, pp. 4465-4470, v 62, No. 12, Washington, DC.
Lawford, H G et al, Conditions that promote production of lactic acid by Zymomons mobilis in batch and continuous culture, Applied Biochemistry and biotechnology, 1998, pp. 173-185, vol. 70-72.

*Primary Examiner*—Nancy Vogel
(74) *Attorney, Agent, or Firm*—Paul J. White; Kenneth Richardson; Mark D. Trenner (57) ABSTRACT

The present invention briefly provides a method of site-specific insertion in *Zymomonas*, comprising, providing a *Zymomonas* gene fragment, interrupting a DNA sequence the fragment, and transforming the *Zymomonas* through homologous recombination with the interrupted fragment.

9 Claims, 11 Drawing Sheets

METHOD OF INACTIVATION OF AN END PRODUCT OF ENERGY METABOLISM IN ZYMOMONAS MOBILIS

The United States Government has rights in this invention pursuant to Contract No. DE-AC36-99GO-10337 between the United States Department of Energy and the National Renewable Energy Laboratory, a division of Midwest Research Institute.

BACKGROUND OF THE INVENTION

1. Field of the Invention

The present invention relates to gene insertion in *Zymomonas mobilis*, and in particular to the insertion inactivation of specific gene products in recombinant *Zymomonas mobilis* strains which ferment xylose and arabinose, or both, into ethanol.

2. Description of the Related Art

Fermentation technology is useful for the conversion renewable biomass cellulose substrates into fuels and chemicals, such as ethanol. A typical substrate is comprised of 35-45% cellulose, 30-40% hemicellulose, and 15% lignin. The hydrolysis fraction contains glucose polymers, and the hemicellulose fraction contains mostly xylose. Arabinose is also a significant fermentable substrate found in biomass materials, such as switchgrass grass and corn fiber.

*Z. mobilis* is widely reported for its ability to rapidly and efficiently convert glucose substrates into ethanol, at a low pH, in an anaerobic culture, and in a medium which contains the inhibitory compounds typically associated with a lignocellulose-hydrolysate. A distinct disadvantage in the use of *Z. mobilis* is, however, that it does not ferment pentose sugars. To overcome this disadvantage, the prior art has focused on recombinant *Z. mobilis* strains which ferment a mixture of glucose, and xylose or arabinose, or both, using exogenous genes which catalyze the metabolism of xylose and arabinose. These strains are based on the use of multicopy plasmids capable of expression of the desired enzyme product.

U.S. Pat. No. 5,514,583 discloses a transformed *Z. mobilis* xylose fermenting strain (CP4/pZB4 and pZB5) having exogenous genes, and plasmid vectors (pZB4 and pZB5) encoding xylose isomerase, xylulokinase, transaldolase and transketolase, and further comprising at least one promoter (Pgap and Peno) recognized by *Zymomonas* which regulates the expression of at least one of said genes. The microorganism is capable of growing on xylose as a sole carbon source, and fermenting xylose to ethanol at about 88% of the maximum theoretic yield. The patent claims an integrated strain.

U.S. Pat. Nos. 5,712,133 and 5,726,053 disclose, inter alia, *Z. mobilis* arabinose fermenting transformants (CP4/pZB 206), containing exogenous genes that encode L-arabinose isomerase, L-ribulokinase and L-ribulose-5-phosphate-4-epimerase, transaldolase and transketolase which impart arabinose to ethanol fermentation capability. The plasmid vector (pZB 206) and a process of using the transformants for the fermentation of a glucose and arabinose containing substrate is also disclosed. The patent claims integration of the exogenous genes into the host genome.

U.S. Pat. No. 5,843,760 discloses a *Z. mobilis* xylose and arabinose fermenting transformant (206C/pZB301) containing exogenous genes encoding xylose isomerase, xylulokinase, L-arabinose isomerase, L-ribulokinase, L-ribulose-5-phosphate 4-epimerase, transaldolase and transketolase, and further comprising at least one promoter recognized by *Zymomonas* which regulates the expression of at least one of said genes, wherein said microorganism is capable of growing on arabinose and/or xylose, alone or in combination, as the carbon source and fermenting said arabinose and xylose to ethanol. The process of using the transformants together with the plasmid vectors (pZB301, pZB401, pZB402, and pZB 403) is also disclosed. This patent claims integration of the exogenous genes into the host genome.

Vital to the engineering of an economic fermentation process for the production of fuels and chemicals, from cellulose containing substrates, is to achieve a high rate of specific product formation and conversion efficiency. When using the pentose-fermenting recombinant strains of *Z. mobilis*, where ethanol is the specific product, the formation of the by-products lactic acid, an end product of energy formation, and xylitol lowers conversion efficiency. Thus, it is desirable to develop new metabolic engineering methods for the site-specific insertion of genes in *Z. mobilis*, such as for the insertion inactivation of lactate dehydrogenase, to enhance the conversion efficiency in a cellulose to ethanol process.

In *Esherichia coli*, the classical method for generating chromosomal inserts of foreign genes involves the use of specialized λ phage cloning vectors that can exist stable in the lysogenic state. Alternatively, site specific genes can be inserted though homologous recombination, when bracketed with *E. coli* chromosomal sequences, or by random transposition if the genes can be cloned in the permissive sites of a transposon. While transposition has been demonstrated in *Z. mobilis*, Pappas, K. M., et al., (1997) Transposon mutagensesis and strain construction in *Zymomonas mobilis*, *Journal of Applied Microbiology*, Vol. 82, p.p. 379-388 (Tn5 or mini Mµ transposition of auxotrophy or antibiotic resistance for genetic analysis in *Z. mobilis*) transposition is random and homologous recombination in *Z. mobilis* has not been demonstrated. Further, no bacteriophage has ever been isolated from *Zymomonas*.

In view of the foregoing, a need exists for a method of site specific insertion in *Z. mobilis*. One practical application of the method would be for the elimination in the formation of by-products, in a *Z. mobilis* fermentation, through the construction of stable recombinant strains, characterized by the insertion inactivation of genes encoding those enzymes in the specific by-product formation pathway, to be eliminated.

SUMMARY OF THE INVENTION

It is therefore an object of the present invention to provide a method for site-specific insertion in *Z. mobilis*.

It is a further object of the present invention to provide a method of eliminating the formation of by-products in a *Z. mobilis* fermentation through the construction of stable recombinant strains, characterized by insertion inactivation of genes encoding those enzymes in the specific by-product formation pathway, to be eliminated.

It is a further object of the invention to provide a method of insertion inactivation of the lactate dehydrogenase gene in *Z. mobilis* to eliminate the formation of the by-product lactic acid.

To overcome the problems associated with the related art and in accordance with the purpose of the invention, as embodied and broadly described herein, the present invention briefly provides a method of site-specific insertion in *Zymomonas*, comprising, providing a *Zymomonas* gene fragment, interrupting a DNA sequence the fragment, and transforming the Zymomonas through homologous recombination with the interrupted fragment.

Additional advantages of the present invention will be set forth in part in the description that follows and in part will be obvious for that description or can be learned from practice of the invention. The advantages of the invention can be realized and obtained by the method particularly pointed out in the appended claims.

BRIEF DESCRIPTION OF THE DRAWINGS

The accompanying drawings, which are incorporated in and which constitute a part of the specification, illustrate at least one embodiment of the invention and, together with the description, explain the principles of the invention.

DETAILED DESCRIPTION OF THE INVENTION

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All US patents are incorporated by reference as though fully set forth herein.

Reference now will be made in detail to the presently preferred embodiments of the invention, examples of which are illustrated in the accompanying drawings. For the examples described below, "plasmid-bearing strains" refers or relates to those strains and vectors described in the US patents identified in the Description of the Related Art. "Z. mobilis genome, or genomic" means the genes which, in toto, specify all the expressed and potentially expressible with a given Z. mobilis, including native plasmid and chromosomal.

EXAMPLES

The following examples illustrate a homologous recombination method for site specific insertion in Z. mobilis and the practical use of the method for insertion inactivation of an unwanted gene, such as a gene associated with a by-product formation. In the following examples, The putative lactate dehydrogenase (ldh) gene was the target region for illustration of the principles of the present invention. ldh converts pyruvate to lactic acid, a by-product in Zymomonas an ethanol product specific fermentation. Integration of the pentose metabolism genes (Example 2) into the Z. mobilis ldh genome using homologous recombination stabilizes the phenotypic response without the use of antibiotics, or other selective pressure.

E. coli DH5α was used as a host for the construction of the plasmid. Strains of Z. mobilis ATCC 39676 and its derivative 206C (U.S. Pat. No. 5,843,760) were used as recipients in the construction of C25. For example, the construction of strain C25 is disclosed in the co-pending patent application Ser. No. 09/565,233 filed May 1, 2000.

E. coli strains were cultured in LB medium at 37° C. Z. mobilis strains were maintained anaerobically in RM (10 g/L yeast extract, 2 g/L $KH_2PO_4$) supplemented with 20 g/L glucose, D-xylose or L-arabinose, unless otherwise specified. All strains containing plasmids were grown in the presence of tetracycline (Tc) ((10 µg/ml in liquid Z. mobilis, and E. coli; 20 µg/ml in agar for Z. mobilis and 15 µg/ml in agar, or ampicillin (Ap), 100 µg/ml for E. coli)). Chloramphenicol was used at 50 µg/ml, for both liquid and solid media, for E. coli, and at a concentration of 100 µg/ml, for both liquid and solid media, for Z. mobilis.

For regeneration and selection of Z. mobilis transformants, mating plates ((10 g/L yeast extract, 5 g/L tryptone, 2.5 g/L $(NH_4)_2SO_4$, 0.2 g/L $K_2HPO_4$ and 50 g/L sugar)) supplemented with tetracycline or nalidixic acid (20 µg/ml) were used. All agar plates were made with 15 g/L agar.

Plasmid DNA isolation, restriction endonuclease digestion, ligation and transformation, agarose electrophoresis and other recombinant DNA techniques were carried out in accordance with published protocols, Sambrook et al., (1989) *Molecular cloning: a laboratory manual*, Cold Spring Harbor laboratory press, Cold Spring Harbor, N.Y., or the respective reagent manufacture's instructions, were specified, and are well known in the art. Genomic DNA of Z. mobilis was extracted using three-milliliters of overnight cells resuspended in 250 ml of 50 mM Tris-50 mM EDTA buffer. The cells were treated with lysozyme at 37° C. for 30 min 1001 of 5% SDS solution and RNAase (final concentration equal to 20 ng/ml) were then added and incubated for an additional 30 min. A phenol/chloroform extraction was performed twice, to remove the proteins. Genomic DNA was recovered by ethanol precipitation.

Example 1

The following example demonstrates gene insertion and inactivation into the *Zymomonas* genome via a homologous recombination This system is based on the(ldh gene of *Zymomonas* having a tetracycline (Tc) resistant gene insert (ldh:: Tc). Plasmids containing the ldh::Tc cassette were used to transform Z. mobilis, and the resultant Tc resistance transformants were analyzed by Southern hybridization. The results showed that the ldh::Tc cassette had been inserted into the ldh region of the *Zymomonas* genome. Thus, the invention of gene integration based on homologous recombination, in *Zymomonas*, together with targeted integration resulting in an inactivated ldh gene, eliminated lactic acid by-product formation in an ethanol fermentation.

A 1-kb ldh fragment was made by PCR using total DNA of Z. mobilis ATCC39676, as a template. PCR was performed using the PCR kit from Perkin Elmer, and is well known. The primers were designed based on a DNA sequence of Z. mobilis CP4, as published in Yamano I., (1993) *Journal of Berteriology*, Vol. 175, 3926-3933. The primers for ldh were:

5'-TCGCGGATCCGTCTATGCGCGTCG-CAATATTCAGTTCC-3' (SEQ ID NO. 1) 5'-TCGCG-GATCCGTCGCTTGTCTATTAAACAAGCG-CATCCGGC-3' (SEQ ID NO. 2) in which a BamHI site (underlined) was incorporated at the 5' ends of each primer. The PCR product (ldh) was approximately 995 bp in length covering the structural gene of ldh. The PCR product was digested using BamHI and ligated with a pUC19, made linear by digestion with BamHI and dephosphorylated by treatment with calf intestinal phosphatase. The ligated Dna was used to transform E. coli DH5 and restriction analyses of the plasmid DNA from ampicillin-resistant transformants confirmed the presence of the expected plasmid, which is designated as pUC19-LDH. A Tcr gene was then inserted in the NcoI site of ldh in pUC19-LDH. The primers used for Tc' gene were: 5'-CTAGGCGTATCACGAGGCCCTTT-3' (SEQ ID NO. 3) 5'-CTAGGCGGACGCGATGGATATGT-3' (SEQ ID NO. 4)

The template DNA used for synthesizing $Tc^r$ was pBR332. The PCR product of the $Tc^r$ gene was approximately 1400 bp. The PCR product of the $Tc^r$ gene and pUC19-LDH were made linear by digestion with NcoI were both subjected to a treatment with Klenow fragment and ligated, The ligation mixture was transformed to E. coli DH5α and restriction analyses of the plasmid DNA from ampicillin and tetracycline-resistant transformants confirmed the presence of the expected plasmid, designated as pUC10-KDH-$Tc^r$.

A. ldh Inactivation using a Replicative (Shuttle) Vector.

The Tc' gene, bracketed by the ldh sequences, was then cloned into are plicative vector pZB1861 (Cm' a pZB 186 derivative). pZB1861 was constructed by digesting pZB186 (U.S. Pat. No. 5,514,583) using Cla I and BssH II to remove the Tc' gene and ligated with a adapter containing a BamHI site. The sequences of the adapter is: 5'-CGATGATATCG-GATCCG-3' (SEQ ID NO. 5) 3'-TACTATAGCCTAG-GCGCGC-5' (SEQ ID NO. 6)

Figure 1:
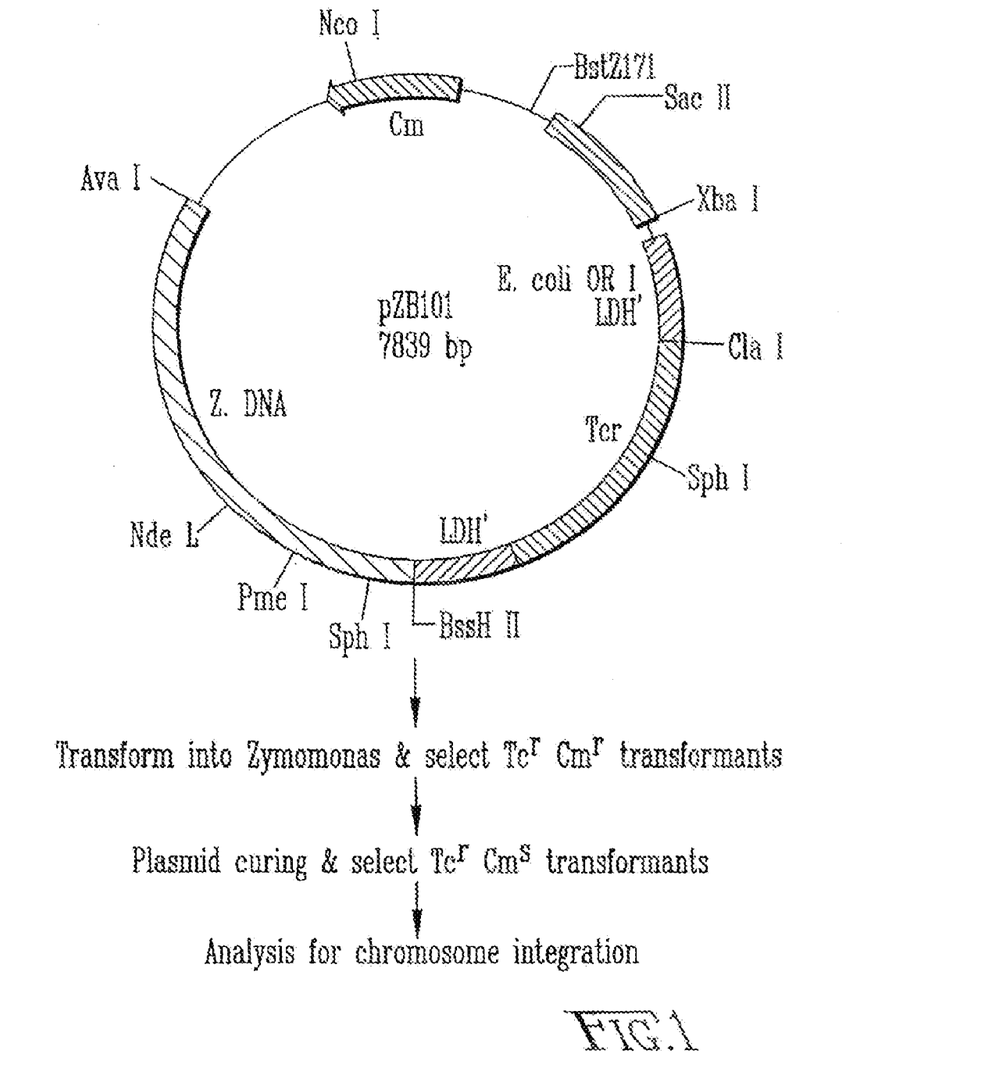
FIG. 1 is a map of the shuttle vector pZB101 (deposited Jan. 11, 2006 under Accession No. PTA-7303 at the ATCC 10801 University Boulevard, Manassas, Va. 20110-2209) and a chart showing the method of using the vector pZB101 according tot he present invention. Homologous recombination is demonstrated using putative lactate dehydrogenase (LDH) gene as the target sequence. The construct LDH:Tc is in a replicative vector pZB 1861:pZB 101/pZB 102.
Figure 2:
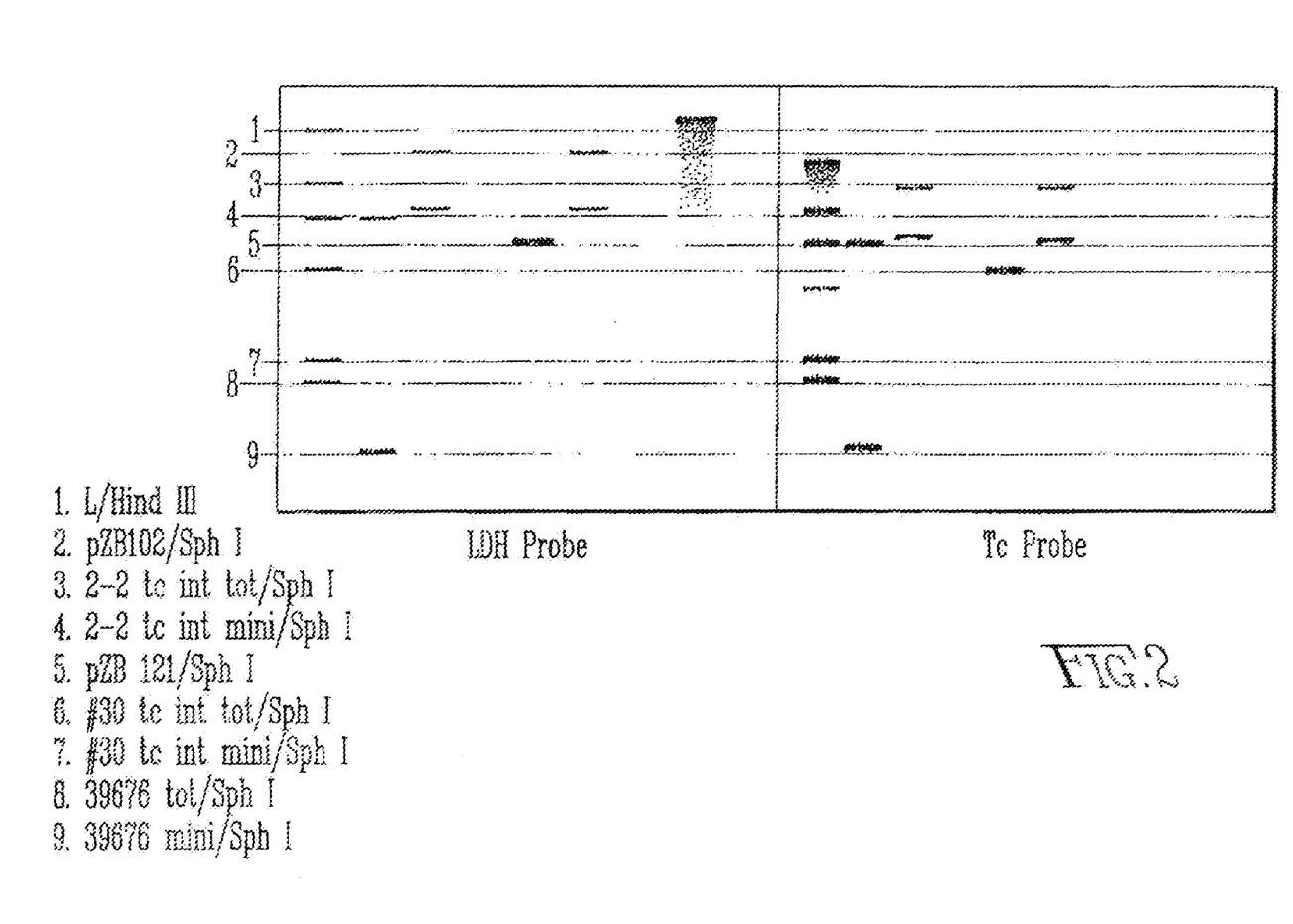
FIG. 2 shows the Southern Analysis of the plasmids pZB 102 and pZB 121 (deposited Jan. 11, 2006 under Accession No. PTA-7303 at the ATCC 10801 University Boulevard, Manassas, Va. 20110-2209) using the Tc probe. The left side of the FIG. (2A) demonstrates results using an ldh probe. The lanes from top to bottom are (1) L/Hindf; (2) pZB102/Sph1; (3)2-2 tc int tot/Sph1; (4) 2-2 tc int mini/Sph1; (5) pZB 121/Sph1; (6) #30 tc int tot/Sph1; (7) #30 tc int mini/Sph1; (8) 39676 tot/Sph1; (9) 39676 mini/Sph1. The right side of the figure (2B) demonstrates results using a Tc probe. The lanes from top to bottom are the same as those indicated for the lanes 1-9 listed for 2(A).

The ligation mixture was transformed to E. Coli DH5a and the $Cm^r$ $Tc^s$ transformants were selected. DNA prepared from the transformants was analyzed and the plasmid, designated pZB1861, lacking the Tcr gene and having a new BamHI site was obtained. The ldh-Tc fragment was excised as a BamH I fragment from pUC19-ldh-Tcr, ligated to pZB 1861 linearized by digestion with BamH I, and dephosphorylated by treatment with calf intestinal phosphatase. The ligated DNA was used to transform E. coli DH5α and restriction analyses of the plasmid DNA from chloramphenicol and tetracycline-resistant transformants confirmed the presence of the plasmid, designated as pZB101 (or pZB 1861-ldh-Tc). The resulting plasmid, pZB101 ($Cm^r Tc^r$) (FIG. 1) was transformed into Z. mobilils 39676. To cure the plasmid, Tcr transformants were inoculated in RMG-Tc tubes (30° C.) followed by a transfer in RMG tubes (37° C.), where the integrates can be selected at elevated temperature which promotes the loss of the plasmid. After approximately 10 transfers (90~100 generations), the cultures were transferred into RMG-Tc10 (30° C.) to enrich the growth of potential $Tc^r$ integrants. The cells were diluted and plated on RMG-Tc20 plates. $Tc^r$ colonies were picked on both RMG-Tc20 and RMG-Cm100 plates. Several $Tc^r$ $Cm^s$ colonies were analyzed for integration of the $Tc^r$ marker by Southern hybridization of the total and plasmid DNA. Probes including DIG-$Tc^r$ and DIG-ldh were used (the probes are shown in Example 2 below). The results showed that all the $Tc^r$ Cms colonies contained the $Tc^r$ marker integrated in ldh gene in the chromosome. See, FIG. 2).

Figure 3:
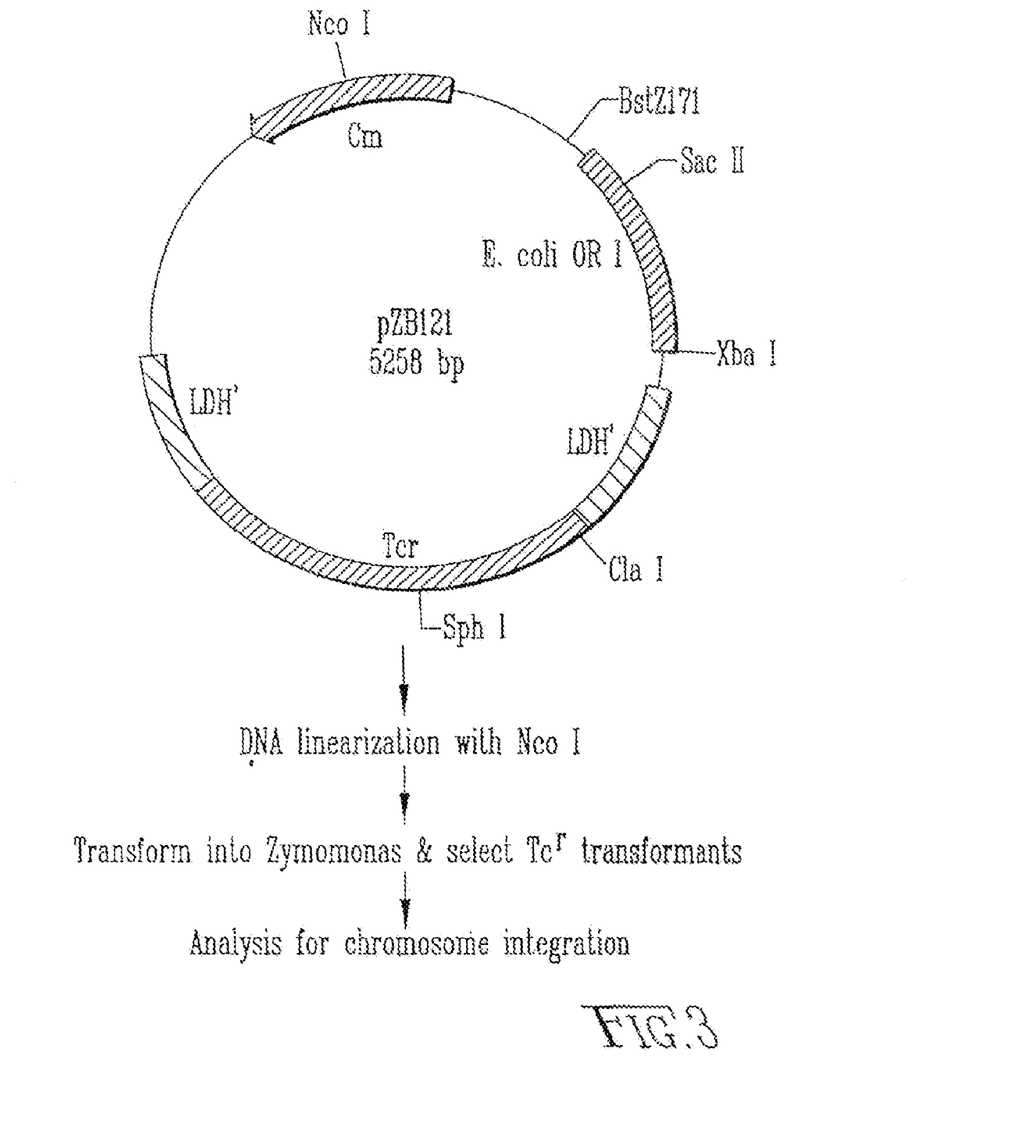
FIG. 3 is a map of the suicide vector pZB121 together with a chart showing the method of using the vector according to the present invention. Homologous recombination is demonstrated using a construct LDH:Tc in a suicide vector pACYC184:pZB 121. DNA is linearized with NcoI. This construct is then used to transform Zymomonas, and then selection for Tc transformants.

B. ldh Inactivation using a Non-Replicative (Suicide) Vector.

pZB101 was digested using Ava I and BssH II to remove the Z. mobilis origin of replication, from the plasmid, and then an intra-molecular ligation on the E. coli origin of replication containing backbone was made. In that procedure, the Ava I and BssH II fragment of pZB101, containing the E. coli origin of replication, was gel-purified and then filled in by a treatment using Klenow fragment. Intramolecular ligation then resulted in a suicide plasmid, designated as pZB121. See, FIG. 3. *Z. moblils* 39676 was transformed by electroporation using either supercoiled pZB121 or pZB121 linearized by digestion using NcoI. Recombinant cells were selected from mating plates containing 20 µg/ml of Tc. The resulting colonies were replica picked onto RMG-Tc and RMG-Cm plates. Only one colony out of 250 analyzed was Tc$^r$ Cm$^s$. Southern hybridization confirmed a double-crossover event in isolate #30.

Figure 4A:
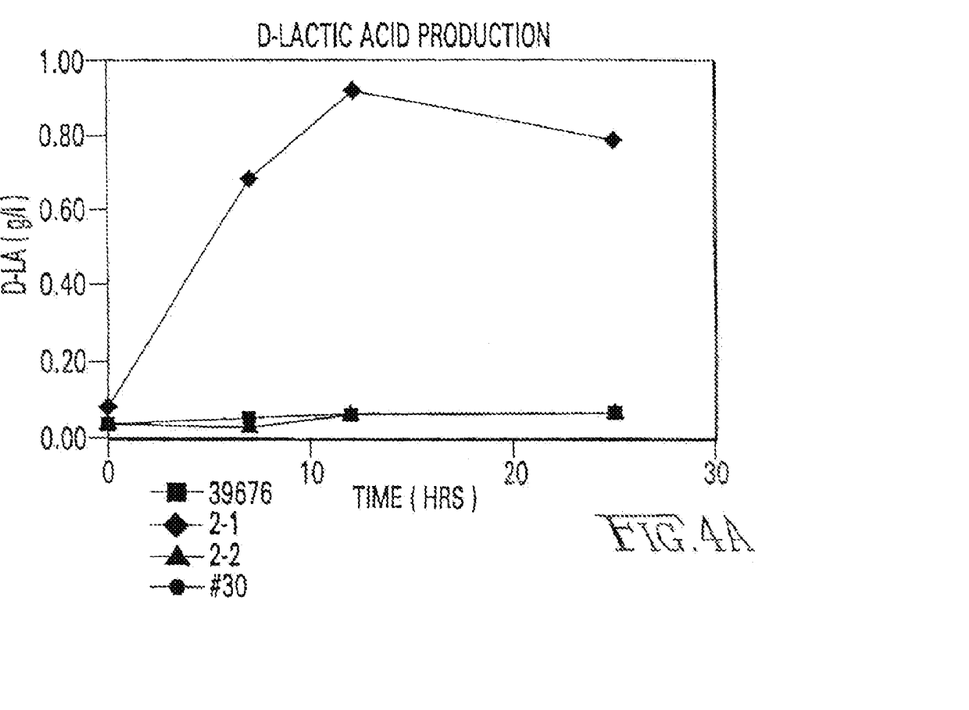
FIGS. 4(A) and FIG. 4(B) show the production of lactic acid in fermentations using strains 2-1, 2-2 and #30, created according to the method of the invention, compared to the wild-type strain 39676. The graph shows that lactic acid production was eliminated using homologous recombination in the ldh (FIG. 4B) gene.
Figure 4B:
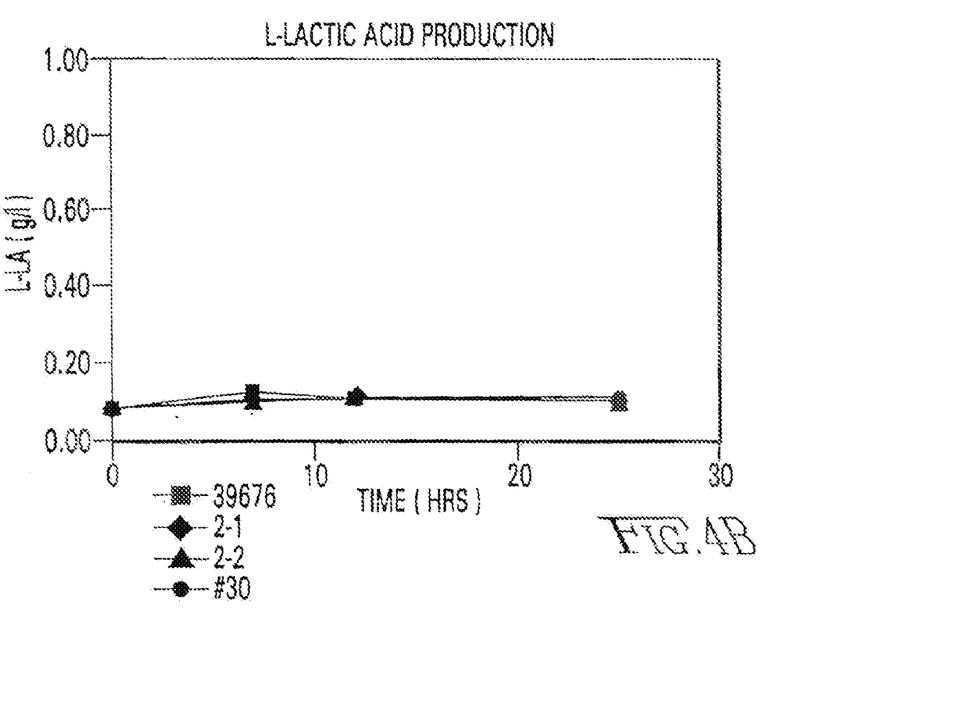

D- or L-lactic acid production was measured in ethanol fermentations using the above shuttle and suicide vector integrants. These tests were conducted in RM containing 10% glucose at 30° C., pH6.0, in 500-ml chemostats for *Z. mobilis* wild type strain 39676 and 4 of the integrants ((including 2-1, 2-2 (from shuttle vector integration) and #30 (from suicidal vector integration)). Samples were taken periodically for HPLC analysis and Boehringer Mannheim Kit analysis (more completely described in Example 2 below). The results demonstrated that 39676 produced D-lactic acid and the production of this by-product was eliminated through integration of Tcr marker in the ldh gene in the integrants (FIG. 4).

In the foregoing example, construction of the ldh integrative cassette, by insertion of a Tc resistance gene into a convenient NcoI site, is shown. However, it is within the scope of the invention to construct an ldh integrative cassette without a restriction site. In this manner the cassette could be made using either PCR fusing methodology, such as the PCR mediated overlap extension technique described in U.S. Pat. No. 5,514,583 to insert gene of interest into the ldh gene, or to create a deleted/inactivated gene by PCR. These products would then be used to obtain *Z. mobilis* strains having an inactivated ldh, and no lactic acid formation.

Example 2

The following example demonstrates the introduction of the arabinose assimilation enzymes in the genome of C25 through homologous recombination via ldh resulting in the inactivation of the lactate dehydrogenase gene of the lactic acid by-product energy metabolism pathway.

Plasmid DNAs were transformed into either *Z. mobilis* or *E. coli* cells by electroporation (Zhang et al., 1995)) Plasmid pZB1862-ldhL-ara, described below, was used to transform *Z. mobilis* or *E. Coli* by electroporation. Transformants were selected on mating plates supplemented with glucose and tetracycline. Tc$^r$ colonies were further confirmed to be Ara$^+$Xyl$^+$ by growth on RM supplemented with xylose or arabinose (RMS and RMA).

Previous attempts to integrate araBAD in the *Zymomonas* chromosome, using the above 1-kb ldh fragment as the homologous region, did not succeed. In order to increase the recombination frequency, a larger homology region was used. A 2.5-kb DNA fragment, which includes ldh and the flanking region was amplified using Pfu PCR. The primers were designed based on the DNA sequence of *Z. mobilis* CP4, published in Yomano et seq. Although a 2.5-kb fragment was expected from PCR, according to the published sequence, a 3.4-kb fragment was obtained instead. After digesting the 3.4-kb fragment with BamHI, two fragments (2.5 and 0.9 kb) were obtained. Both fragments were tested by PCR, using primers designed to anneal to only the ldh. The 2.5-kb fragment produced a PCR product of the correct size, whereas the 0.9-kb fragment did not, indicating that the former contained the ldh sequence. Therefore, the 2.5-kb BamHI fragment (designated ldhL) was cloned and used as the homologous region for gene integration into C25.

The ldhL fragment and digoxygenen (DIG)-labeled ldh and ara probles were amplified by PCR using either Pfu (Stratagene, La Jolla, Calif.) or Taq DNA polymerase (Qiagen, Valencia, Calif.). DIG-UTP was purchased from Boehringer Mannheim, Indianapolis, Ind. PCR products for ldhL, ldh, and ara are 2.5, 1, and 1.4 kb, respectively. The following primer sequences were used:

ldhL: 5'-TCGCGGATCCTCTATCCCTTTATTTTTC-TATCCCCATCACCTCGG-3' (SEQ ID NO. 7)
5'-TCGCGGATCCGCGGCTGACATACATCT-TGCGAATATAGGG-3' (SEQ ID NO. 8)

DIG-ldh: 5'-TCGCGGATCCGTCTATGCGCGTCG-CAATATTCAGTTCC-3' (SEQ ID NO. 1)
5'-TCGCGGATCCGTCGCTTGTCTATTAAA-CAAGCGCATCCGGC-S' (SEQ ID NO. 2)

DIG-ara: 5'-CTAACATGTTGACTCCTTCTCTAGACT-TAGCG-3' (SEQ ID NO. 9) 5'-GTTGAAAC-CGCTGGGCACCACGC-3' (SEQ ID NO. 10)

Figure 5:
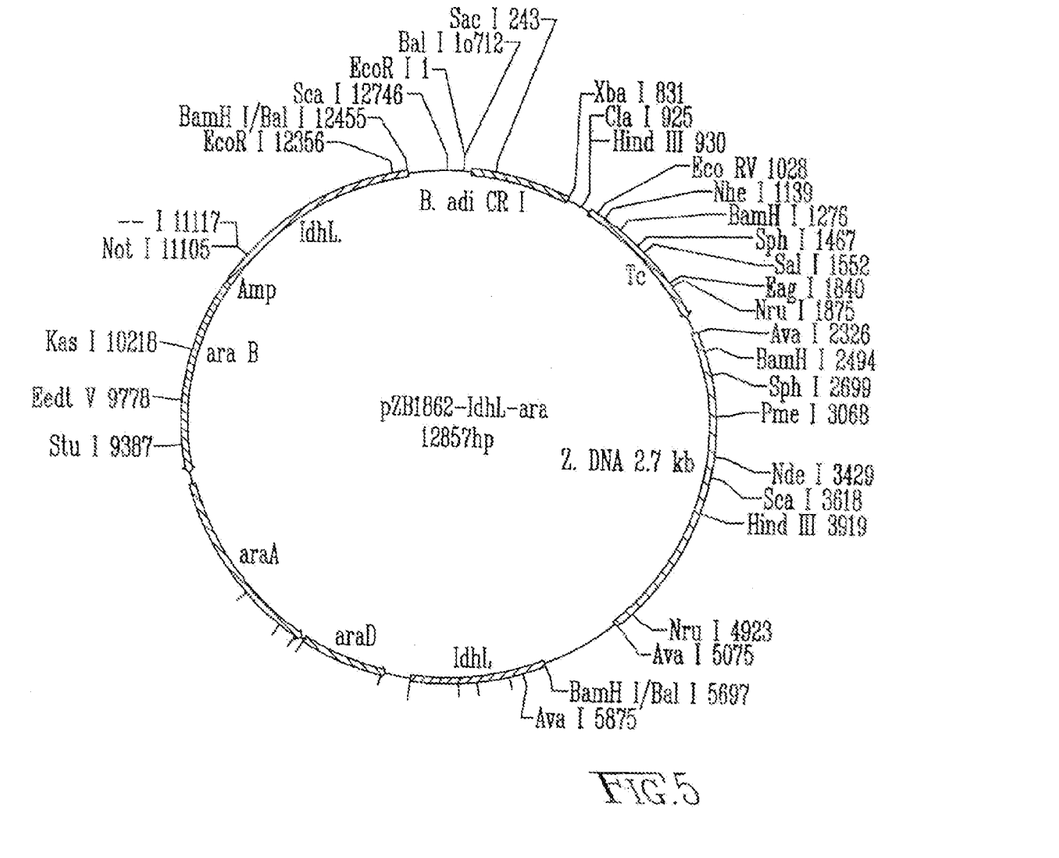
FIG. 5 is a map of the integrative plasmid pZB 1862-IdhL-ara, Patent Deposit Designation PTA-1798 deposited at American Type Culture Collection, Manassas, Va. 20110-2209 USA on May 2, 2000. All restrictions on availability will be removed upon issuance of the rejected claims in a patent. The araBAD is inserted in the NotI site of ldhL disrupting ldh. The construction is based on the replicative plasmid pZB1862 of Z. mobilis. Plasmid pZB1862 is a derivative of pZB186, a plasmid disclosed in U.S. Pat. Nos. 5,514,583 and 5,712,133, incorporated herein by reference.
Figure 6A:
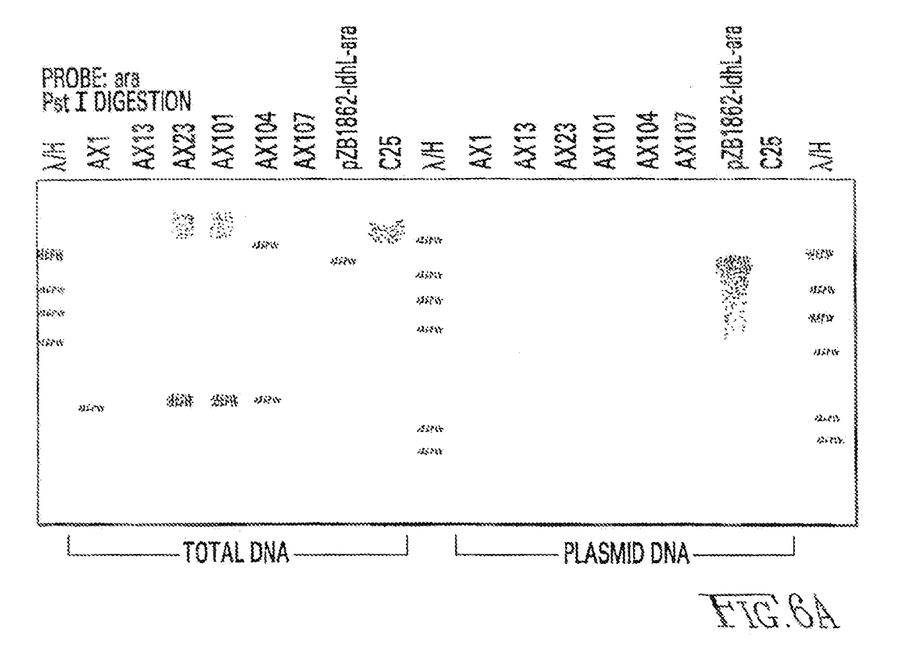
FIG. 6(A) (Probe: ara PsI digestion) and FIG. 6(B) (Probe: ldh Pstl digestion) show the Southern analysis of the chromosomal integrated xylose/arabinose-fermenting Z. mobilis strains from homologous recombination using DIG-ara abd DIG-ldh probes. AX1, 13, 23, 101, 104, and 107 are araBAD integrants. C25 is the host control pZB 1862-ldhL-ara is the plasmid control isolated from DH5α. λ/H is a molecular wright marker: 23, 9.4, 6.6, 4.3, 2.3 and 4.0 kb.
Figure 6B:
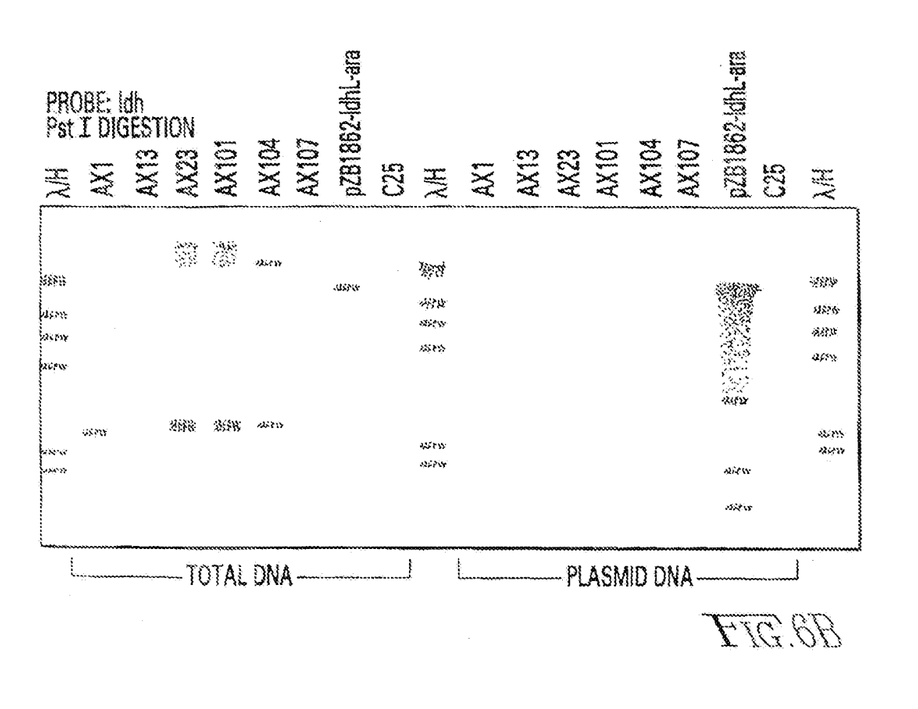

For cloning purposes, a NotI site was introduced in ldhL by insertion of an oligonucleotide 5'CATGCGCGGC-CGCC-3' (SEQ ID NO. 11) at NcoI site, which is located in the middle of the ldh gene. The new NotI site was approximately 1.4 and 1.1 kb from either end of ldhL. A BamHI fragment of ldhL (2.5 kb) containing the NotI site was ligated into pZB1862 at a Bc/I site. Finally, a 4.4-kb Pgap-araBAD, isolated from pZB206 (U.S. Pat. Nos. 5,712, 133 and 5,726,053), was cloned into the NotI site, of ldhL, to form the integrative plasmid, pZB1862-ldhL-ara. See FIG. 5.

The Pgap-araBAD operon, containing the three arabinose-assimilating genes, was integrated into the ldh site in the C25 chromosome through homologous recombination. To integrate the araBAD genes into the genome of C25, pZB1862-ldhL-ara was constructed in *E. coli* DH5α. The plasmid pZB1862-ldhL-ara was transferred into C25 by electroporation. The Tc resistant transformants were selected and tested for growth on arabinose. During propagation of the transformants, Pgap-ara-BAD could be integrated in the chromosome of C25 by the replacement of ldhL with the ldhL'-araBAD-ldhL' cassette (from the plasmid) through homologous recombination.

To enrich and isolate the integrants, plasmid curing was conducted for the transformants. Plasmid pZB1862-ldhL-ara will replicate in *Z. mobilis*. However, *Z. mobilis* tends to lose foreign plasmids at sub-optimal growth conditions (e.g. 37° C.). Using this characteristic, curing of pZB1862-ldhL-ara was achieved by subculturing C25 transformants at 37° C. in the absence of Tc for several transfers. Cultures form each transfer were constantly monitored of for the loss of the plasmid. By the third transfer, 100% of the cells became Tc$^s$, indicating a loss of the plasmid. Cultures from the 3$^{rd}$, 4$^{th}$, 5$^{th}$, and 6$^{th}$ transfers were inoculated in RM containing arabinose (RMA), at 30° C., to enrich the growth of potential Pgap-araBAD integrants. The enriched cells were transferred to RMG plates and replica-picked onto RMA, RMX, and RMGTc plates. Several integrants (AX) with the phenotype of Xyl$^+$Ara$^+$Tc$^s$ were subjected to further analysis, as described below. These integrants were able to use either xylose or arabinose as a sole carbon source.

Figure 7A:
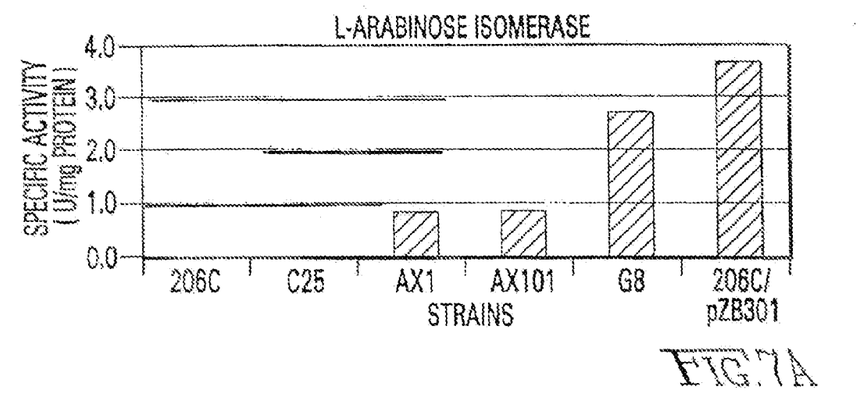
FIG. 7(A), FIG. 7(B) and FIG. 7(C) represent bar graph results of the enzymatic activities of L-arabinose isomerase (FIG. 7A), L-ribulokinase (FIG. 7B) and ribulose-5-phosphate (FIG. 7C).
Figure 7B:
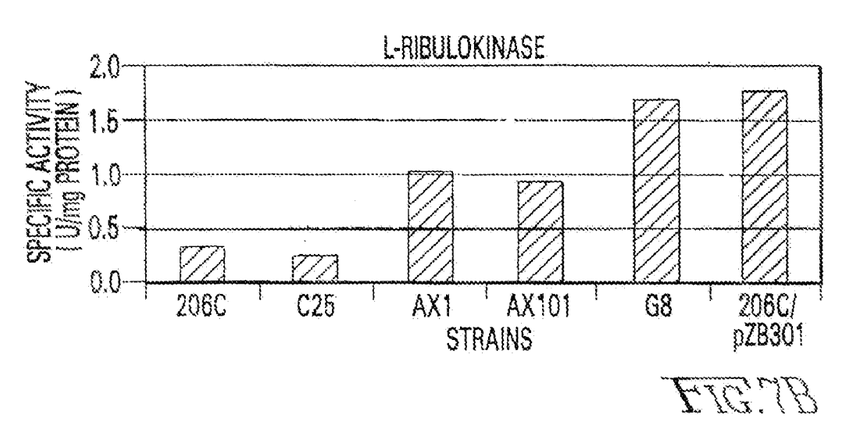
Figure 7C:
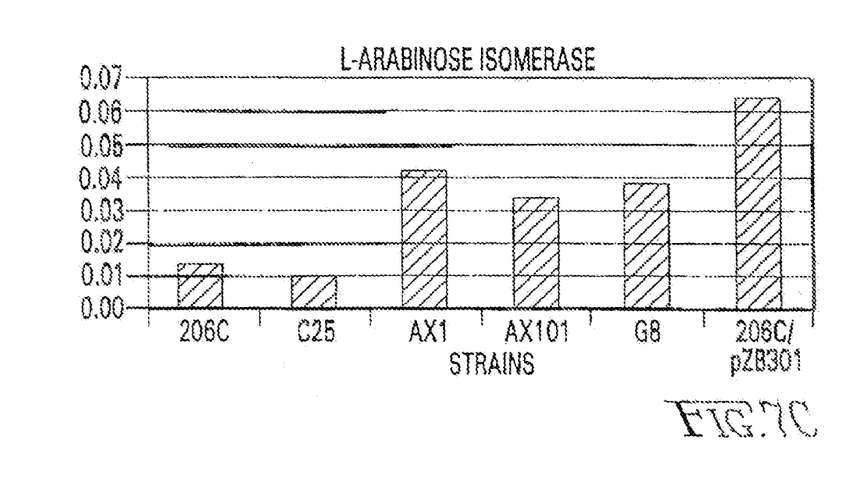

Integration of Pgap-araBAD in ldh of C25 was confirmed by Southern hybridization, for the integrants DNA using the DIG-labeled ara and ldh probes. See, FIGS. 6(*a*) and (*b*). There is only one PstI site on pZB 1862-ldhL-ara and it is located in Pgap-araBAD. Therefore, one hybridizaion band (12.9 kb) from the PstI-digested plasmid was expected, using the ara probe. With Pgap-araBAD integrated in the genome two bands generated by the PstI site in PgaparaBAD and the adjunct PstI sites on the chromosome located outside the Pgap-araBAD were expected. The results from FIG. 7(a) clearly showed that two bands form the total DNA preparation hybridized with the ara probe and demonstrated integration of Pgap-araBAD. The lack of hybridization bands from plasmid DNA of integrants indicated that integration had occurred on the chromosome, rather than on native plasmids. To show that the ldh was disrupted by the Pgap-araBAD integration, the same DNA was transferred and hybridized with the ldh probe. As expected, the hybridization patterns for the integrants were exactly the same on both blots, except for C25, as shown in FIG. 7(b). The total DNA from the host strain, C25, used for Pgap-araBAD integration, which has an intact ldh, showed only one band. The results confirmed that araBAD was integrated in ldh of C25.

Xylose isomerase (XI), xylulokinase (XK), L-arabinose isomerase (L-AI), L-ribulokinase (L-RK), L-ribulose-5-P-4-epimerase (L-Repi), transketolase(TKT) and transaldolase (TAL) were assayed, using cell-free extracts of the Z. mobilis integrants and control strains, according to Zhang, et al., 1995; and Deanda et al., 1996, with minor modifications. Cell-free extracts were prepared by collecting the cultures at late-log phase (30° C., $OD_{600}$ approximately 1.2), washing once with sonication buffer (10 mM Tris-HCl, pH 7.6 10 mM $MgCl_2$) and sonicating. The cell debris was removed by centrifugation (14,000 rpm, 45 min 4° C.). In the L-AI assay, the volumes of timed samples were scaled down by half (50 µl), 70% $H_2SO_4$ (1.5 ml) and 0.12% carbazole (50 µl). All of the tubes were maintained in a 25° C. water bath, both before and after the addition of 70% $H_2SO_4$, until reading the absorbency. The samples were taken at 0, 5, 10, and 20 min during the reaction.

Figure 8:
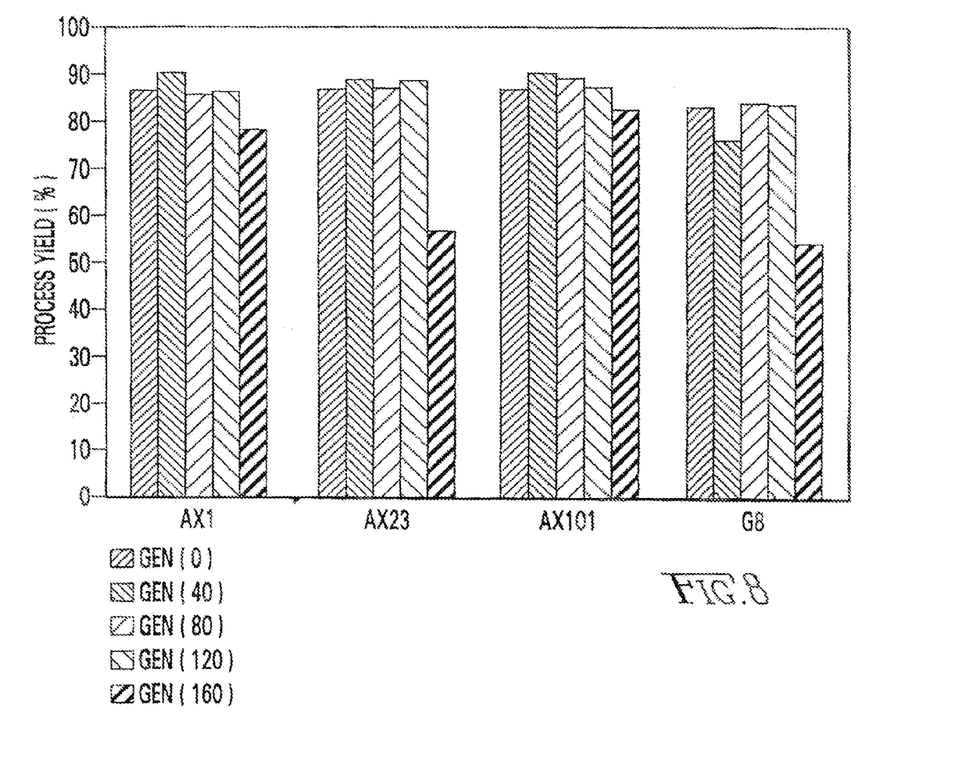
FIG. 8 represents a bar graph result of the ethanol process yields of the chromosomal integrated xylose and arabinose-fermenting Zymomonas strains on RMGXA (1:2:2%) at T=30° C., without pH control. These strains were inoculated form cultures at various generations on non-selective media.
Figure 9A:
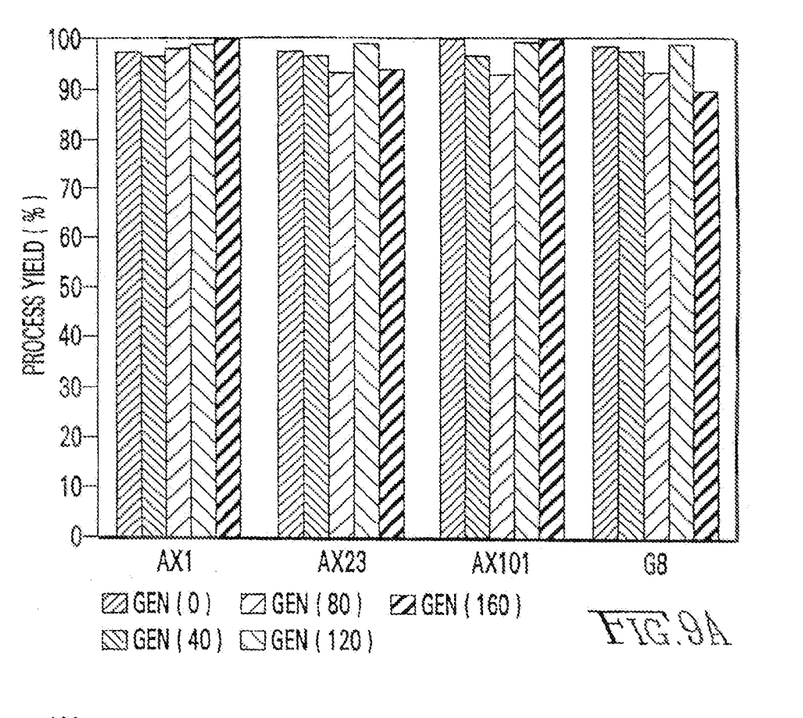
FIG. 9(A) (xylose utilization %) and FIG. 9(B) show bar graph results for xyklose and arabinose utilization of the chromosomal integrated xylose and arabinose-fermenting Zymomonas strains on RM containing 1% glucose, 2% xylose and 2% arabinose at 30° C. with pH control. These strains were inoculated from cultures at various generations on non-selective media.
Figure 9B:
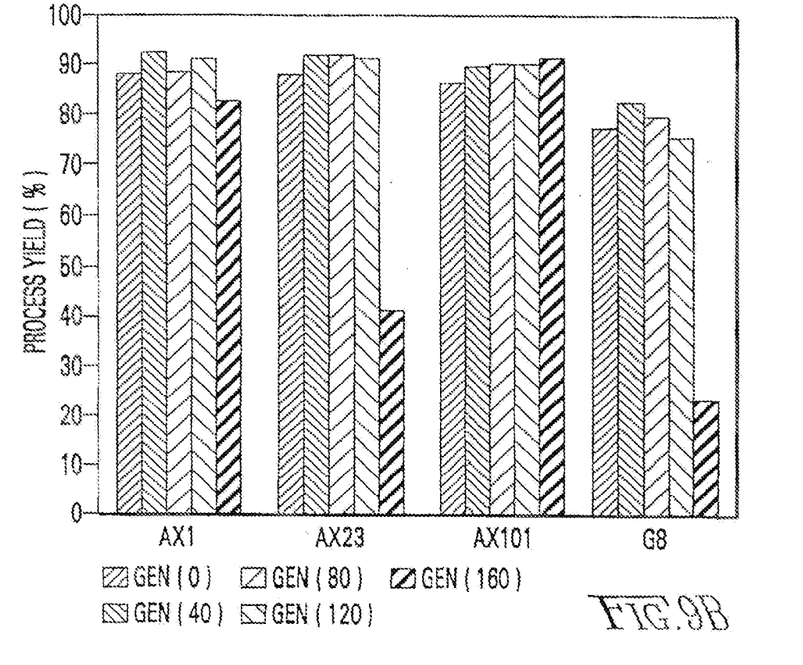
Figure 10A:
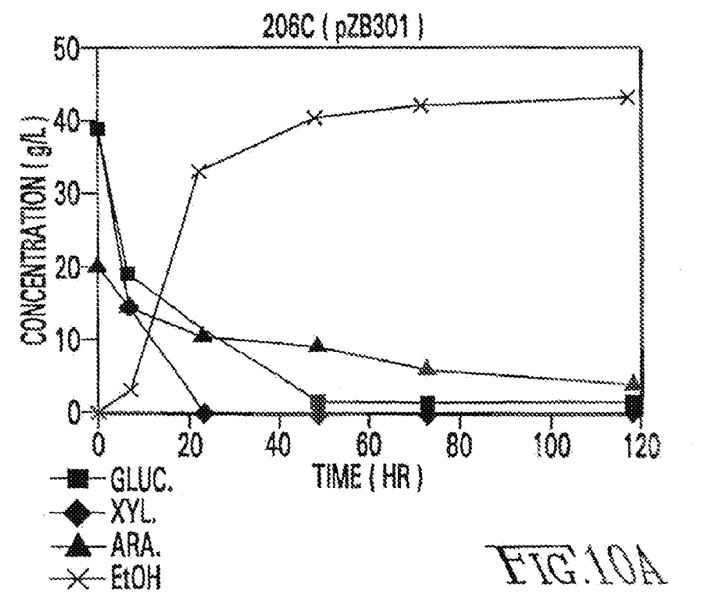
FIG. 10(A) (strain 206C (pZB301), FIG. 10(B) (strain AX1), FIG. 10(C) (strain AX101), and FIG. 10(D) (strain G8) are line graph representations of the fermentation performance of the chromosomal integrated xylose and arabinose-fermenting Zymomonas strains in RM containing 4% glucose, 4% xylose and 2% arabinose at pH 5.5 and 30° C. (glucose=diamond; xylose=square; arabinose=triangle; ethanol is represented with an "x").
Figure 10B:
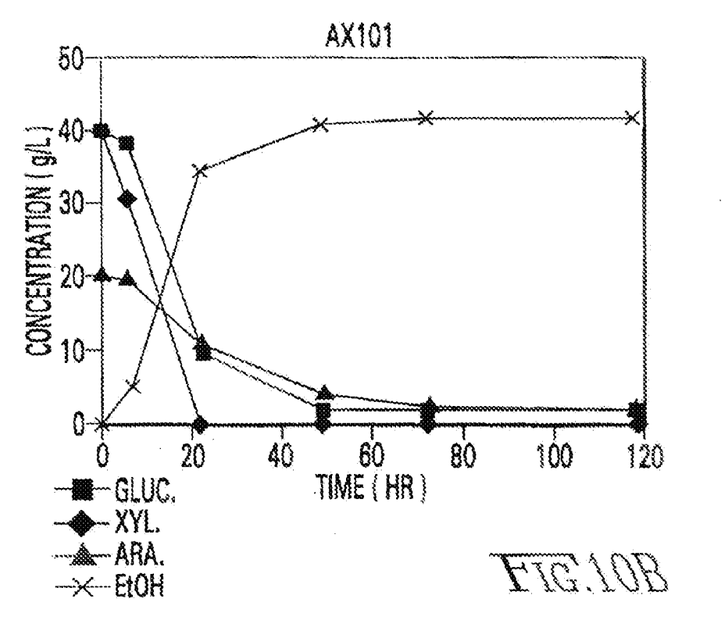
Figure 10C:
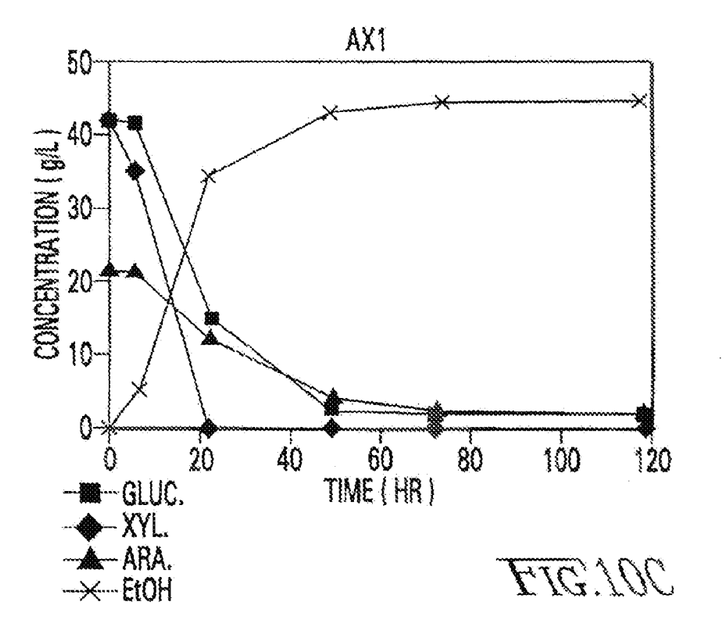
Figure 10D:
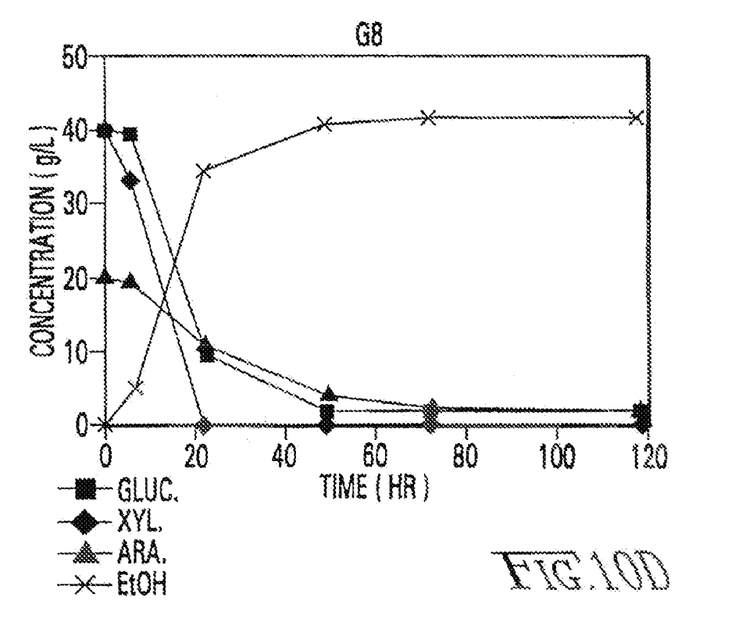

Although the integrants, from homologous recombination were able to grow on D-xylose and L-arabinose, the expression level of the integrated genes it was determined by measuring enzymatic activity. Isolates C25/AX1, C25/AX101, and C25/G8 were chosen for the enzymatic assays because they were the most stable integrants, as determined in the stability studies described below. The results of the enzymatic assays for L arabinose Isomerase, L-Ribulokinase, and L Ribulose-5-Phosphate-4-Epimerase are summarized in FIG. 8 (other enzymes not shown). For all assays (with and exception of xylulokinase), integrants showed positive activities as compared to the controls (C25 and/or 206C). It is believed, at this moment, that the low activity of XK for the integrants, might be due to experimental error, the nature of the assay, or both. In most assays, (excluding L-ribulokinase and xylose isomerase), the integrants showed lower activities than the plasmid-bearing strain (206C/pZB301). This is presumable related to the copy number of the genes.

For stability studies, the cultures were inoculated into test tubes containing RMG, incubated overnight at 30° C., and transferred daily to RMG tubes. The inoculum was controlled to allow transfer every 10 generations. At every 40 generations, the cells were used to inoculate flasks, containing a mixture of sugars, to test the fermentation capabilities on the sugars without pH control at 30° C. Batch fermentation studies were performed at 30° C. with pH control in Bio-StatQ chemostats, a trademark of B. Braun, Allentown, Pa., using 500 ml as the working volume. The pH was automatically controlled with 2N KOH. Initial sugar concentration and pH varied between each batch, depending on the culture conditions. All the sugars used were reagent grade. Samples were taken periodically throughout the fermentation, and analyzed for sugars, ethanol and by-products with HPLC, as described previously (Zhang 1995). Optical density, at 600 nm (OD600), was measured in order to monitor cell growth. Ethanol yield was based on the amount of total available sugar.

Several chromosomal integrated xylose and arabinose fermenting Z. mobilis strains developed through both homologous recombination and transposition were studied for their stability in a non-selective medium (RMG). These strains were cultured in RMG medium and serially transferred, daily, after about 10 generations. After every 40 generations, the cells were used to inoculate a flask containing 1% glucose and 2% xylose and 2% arabinose for examination of their ability to ferment xylose and arabinose to ethanol. Ethanol process yields, and xylose and arabinose utilization rates, were used as the stability trait. Two of the isolates remained stable for 160 generations. Three integrated strains and a plasmid-bearing strain were further tested for fermentation performance, in a media containing a mixture of 4% glucose, 4% xylose, and 2% arabinose at pH 5.5 and 30° C. As shown in FIG. 10, all three strains utilized glucose, xylose and arabinose in 72 hours, while the plasmid-bearing strains still had 6 g/L residual arabinose. However, the integrated strains produced more xylitol (4 µl) than the plasmid bearing strain (1 g/L). The two homologous recombination AX1 and AX101 strains did not produce lactate because the lactate dehydrogenase gene was inactivated through the gene integration. The process yields (about 83% of theoretical) of the integrated strains were very similar to the plasmid bearing strain. Moreover, the integrated strains grew to a greater cell densities, which is probably due to a the lesser metabolic burden associated with having only singly copy of the seven genes.

While the present invention has been described in connection with the illustrated embodiments. It will be appreciated and understood that modifications may be made without departing, from the true spirit and scope of the invention.

We claim:

1. A method of site specific insertion or deletion in *Zymomonas* comprising:
    (a) providing a Zymornonas DNA fragment;
    (b) interrupting a sequence in the *Zymomonas* DNA fragment to provide an interrupted sequence formed of a first component part and a second component part of the *Zymomonas* DNA fragment;
    (c) recombining the interrupted sequence with a desired sequence to form a recombinant gene fragment wherein the first component part and the second component part of the Zyrnornonas DNA fragment respectively flank the desired sequence to facilitate site specific insertion or deletion, the first component part and the second component part targeting a by-product of a *Zymomonas* metabolic pathway; and
    (d) transforming the *Zymomonas* to induce site specific insertion or deletion by homologous recombination with the interrupted sequence to provide a recombinant *Zymomonas*, wherein said recombinant gene fragment provides for elimination of a by-product of a metabolic pathway in the recombinant Zymomon as; and further comprising
    (e) ligating the interrupted sequence with a plasmid vector; wherein the step (d) of the transforming the Z. *mobilis* organism occurs through homologous recombination with the interrupted sequence of the plasmid vector; wherein the plasmid is selected from the group consisting of pZB 101, pZB 102, and pZB 121.

2. The method of claim 1 wherein the DNA fragment used in the providing step (a) encodes a structural protein in a metabolic pathway of the by-product to be eliminated.

3. The method of claim 1 wherein the recombining step (c) comprises inserting a DNA sequence inside the DNA fragment.

4. The method of claim 1 wherein the interrupting step (b) and the recombining step (c) result in site-specific deletion in the transforming step (d).

5. The method of claim 2 wherein the by-product to be eliminated is lactic acid.

6. The method of claim 3 wherein the desired sequence used in the recombining step (c) comprises a selection marker.

7. The method of claim 3 wherein the desired sequence used in the recombining step (c) comprises an operon encoding at least one protein selected from the group consisting of xylose isomerase, L-ribuloltinase, L-ribulose-5-phosphate 4-epimerase, transaldolase or transketolase, and a promoter for expression of the structural gene in *Zymomonas*.

8. The method of claim 1 further comprising a step of curing the *Zymomonas* of the plasmid.

9. A method of site specific insertion or deletion in *Zymomonas mobilis* comprising:
 (a) providing a *Zymomonas mobilis* DNA fragment;
 (b) interrupting a sequence in the *Zymomonas mobilis* DNA fragment to provide an interrupted sequence formed of a first component part and a second component part of the *Zymomonas mobilis* DNA fragment;
 (c) recombining the interrupted sequence with a desired sequence to form a recombinant gene fragment
 wherein the first component part and the second component part of the *Zymomonas mobilis* DNA fragment respectively flank the desired sequence to facilitate site specific insertion or deletion, the first component part and the second component part targeting a by-product of a *Zymomonas mobilis* metabolic pathway;
 (d) transforming the *Zymonomas mobilis* to induce site specific insertion or deletion by homologous recombination with the interrupted sequence to provide a recombinant *Zymomonas mobilis*, wherein said recombinant gene fragment provides for elimination of a by-product of a metabolic pathway in the recombinant *Zymomonas mobilis* and;
 (e) ligating the interrupted sequence with a plasmid vector; wherein the step (d) of the transforming *Z. mobilis* organism occurs through homologous recombination with the interrupted sequence of the plasmid vector; wherein the plasmid is the integrative plasmid pZB1862-ldhL-ara that effects site-specific homologous recombination into said *Z. mobilis* organism at the ldhL gene to introduce components of the arabinose operon.

* * * * *

SEQUENCE LISTING

<160> NUMBER OF SEQ ID NOS: 11

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 1

```
tcgcggatcc gtctatgcgc gtcgcaatat tcagttcc                    38

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 2
tcgcggatcc gtcgcttgtc tattaaacaa gcgcatccgg c                41

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 3
ctaggcgtat cacgaggccc ttt                                    23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 4
ctaggcggac gcgatggata tgt                                    23

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Adapter
      sequence

<400> SEQUENCE: 5
cgatgatatc ggatccg                                           17

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Adapter
      sequence

<400> SEQUENCE: 6
cgcgcggatc cgatatcat                                         19

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 7
tcgcggatcc tctatcccttt tatttttcta tccccatcac ctcgg           45

<210> SEQ ID NO 8
```

-continued

```
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 8
tcgcggatcc gcggctgaca tacatcttgc gaatataggg                            40

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 9
ctaacatgtt gactccttct ctagacttag cg                                    32

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 10
gttgaaaccg ctgggcacca cgc                                              23

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
catgcgcggc cgcc                                                        14
```